United States Patent [19]

Blidschun et al.

[11] Patent Number: 4,680,163

[45] Date of Patent: Jul. 14, 1987

[54] PROCESS AND APPARATUS FOR STERILIZING CONTAINERS

[75] Inventors: Benno Blidschun, Herford; Ernst G. Lierke, Schwalbach, both of Fed. Rep. of Germany

[73] Assignee: Kolbus GmbH & Co. KG, Rahden, Fed. Rep. of Germany

[21] Appl. No.: 721,311

[22] Filed: Apr. 9, 1985

[30] Foreign Application Priority Data

Apr. 14, 1984 [DE] Fed. Rep. of Germany ....... 3414268
Nov. 2, 1984 [DE] Fed. Rep. of Germany ....... 3440014

[51] Int. Cl.$^4$ .......................... A61L 2/18; A61L 2/26
[52] U.S. Cl. ..................................... 422/28; 422/302; 239/3; 239/132.1; 239/135; 239/288
[58] Field of Search .............. 422/22, 28, 29, 34, 422/302, 303; 53/426; 239/3, 132.1, 135, 288, 706-708

[56] References Cited

U.S. PATENT DOCUMENTS

| | | | |
|---|---|---|---|
| 2,826,513 | 3/1958 | Blanchard | 239/3 |
| 3,090,745 | 5/1963 | Berghaus | 55/107 |
| 3,516,608 | 6/1970 | Bowen et al. | 239/135 |
| 3,723,060 | 3/1973 | Lisiecki | 422/302 |
| 3,807,634 | 4/1974 | Vogt | 239/288 |
| 4,099,914 | 7/1978 | Gustafsson et al. | 53/426 |
| 4,296,068 | 10/1981 | Hoshino | 422/62 |
| 4,424,189 | 1/1984 | Hick | 422/302 |
| 4,516,521 | 5/1985 | Szelagowski et al. | 239/288 |
| 4,544,570 | 10/1985 | Plunkett et al. | 239/3 |
| 4,545,525 | 10/1985 | Sacher et al. | 239/3 |

FOREIGN PATENT DOCUMENTS

| | | |
|---|---|---|
| 949253 | 9/1956 | Fed. Rep. of Germany . |
| 1109320 | 6/1961 | Fed. Rep. of Germany . |
| 2136934 | 1/1973 | Fed. Rep. of Germany . |
| 2435940 | 2/1975 | Fed. Rep. of Germany . |
| 2606037 | 8/1977 | Fed. Rep. of Germany . |
| 2744637 | 4/1978 | Fed. Rep. of Germany . |
| 2300883 | 6/1979 | Fed. Rep. of Germany . |
| 2741996 | 4/1980 | Fed. Rep. of Germany . |
| 3049244 | 7/1982 | Fed. Rep. of Germany . |
| 3047087 | 7/1982 | Fed. Rep. of Germany . |
| 3235476 | 5/1983 | Fed. Rep. of Germany . |
| 3229383 | 2/1984 | Fed. Rep. of Germany . |
| 2089213 | 6/1982 | United Kingdom . |

OTHER PUBLICATIONS

Entwicklungstendenzen bei der Desinfektion in der Lebensmittelindustrie, Dr. H. Mrozek, 12/1982, pp. 348-352.
Keng-Wutu et al, A High-Capacity Condensation Aerosol Generation System, Environmental Science & Technology (USA), vol. 13, pp. 698-701, 1979.

Primary Examiner—David L. Lacey
Attorney, Agent, or Firm—Chilton, Alix & Van Kirk

[57] ABSTRACT

Open-topped containers are sterilized by employing an electrostatic field to insure complete coating of the interior surface of such containers with a sterilizing agent. The sterilizing agent is supplied in liquid form, ultrasonically atomized, the thus formed droplets entrained in a stream of carrier gas and an electrical charge imparted to the entrained droplets so that they will be influenced by the electrostatic field created in the containers.

31 Claims, 4 Drawing Figures

PROCESS AND APPARATUS FOR STERILIZING CONTAINERS

BACKGROUND OF THE INVENTION (1) Field of the Invention

The present invention relates to the sterilization of containers and particularly to a wet aseptic technique for rendering plastic containers virtually free of live micro-organisms whereby such containers are suitable for use in the storage of food stuffs. More specifically, this invention is directed to sterilizing apparatus and especially to apparatus for reliably and substantially completely coating the interior surfaces of open-topped pots and the like with a material which functions as a germicidal agent. Accordingly, the general objects of the present invention are to provide novel and improved methods and apparatus of such character.

(2) Description of the Prior Art

While not limited thereto in its utility, the present invention is particularly well-suited for use in the sterilization of open-topped plastic containers of the type which are commonly employed in the retail distribution of dairy products. In order to render the use thereof practical, such containers must be treated so as to be substantially free of live micro-organisms at the time of filling. Micro-organisms, if present, will expedite the spoilage of the product with which the container is filled and thus lead to unacceptably short shelf life. There are a number of techniques available in the prior art for killing micro-organisms in containers destined to receive food-stuffs. These prior art techniques include irradiation with ultraviolet light, use of a pressurized air-steam mixture, use of a sterilizing gas, and the so-called "wet aseptic" processes. In prior art wet aseptic processes the interior wall surfaces of a container to be sterilized are sprayed with an atomized liquid which is unstable in vivo and transient in action in vivo. The sterilizing agents used in prior wet aseptic processes include solutions of hydrogen peroxide, alcohol and chlorine. The spraying step, in prior wet aseptic processes, is followed by drying, typically with a stream of hot air. Wet aseptic processes are disclosed in U.S. Pat. Nos. 3,723,060, 4,099,914, 4,169,123 4,296,068 and 4,424,189.

Of the available prior art sterilizing techniques, the wet aseptic process wherein a peroxide is employed as the sterilizing agent has proved to be highly reliable and containers sterilized by this process have exhibited the maximum period in which food-stuffs may be stored without spoiling. The highly effective germicidal action of peroxide is attributable to the fact that atomic oxygen is formed during decomposition of the peroxide. Atomic oxygen exhibits a very strong oxidizing action at the moment of formation and thus is an exceptionally effective bactericide. The organic substances, for example the micro-organisms themselves, actually catalyse and thus take part in the decomposition reaction which results in the formation of the atomic oxygen. The effectiveness of a wet aseptic process employing $H_2O_2$ is further enhanced by the fact that liquid hydrogen peroxide, which condenses on the container surfaces, penetrates into the cells of micro-organisms and causes the destruction thereof.

When a germicidal agent is distributed by spraying, only relatively slight wetting of the interior surface of an open-topped container can be achieved. The inability to obtain complete wetting is attributable to the fact that conventional spray nozzles produce droplets which have diameters in the range of between 50 and 150 $\mu$m. Accordingly, when the droplets form on the surface of a container during a spraying operation, relatively large areas will remain between the droplets and these areas will be unwetted and thus not sterilized. This problem, i.e., the inability to completely wet the surface or surfaces of a container to be sterilized, is aggravated by the facts that it is generally desired to spray only very small amounts of a $H_2O_2$ or similar solution, i.e., 10 to 30 mg per average container, and the containers are typically comprised of a plastic material which is either unwettable or can be wetted only with difficulty.

Subsequent to the spraying step a wet aseptic process wherein peroxide is employed as the germicidal agent, it is common practice to perform a further treatment step to insure that only extremely small amounts of peroxide, which is a toxic substance, will remain on the surfaces of the container. The required removal of the peroxide will be accomplished by the volatilization thereof through the application of heat. Accordingly, when using a wet aseptic process and employing a hydrogen peroxide solution, an after-treatment is invariably required in order to remove unacceptable amounts of peroxide which remain after the sterilization step. Thus, in addition to the inability to obtain absolute sterilization, because of the formation of relatively large droplets as discussed above, the prior art wet aseptic techniques have also been characterized by a comparatively high consumption of energy and by a high consumption of the sterilizing agent itself.

In summary, there has been a long-standing desire in the art to improve the efficiency of wet aseptic sterilizing techniques and particularly to insure that substantially the entire surface of a container to be sterilized is wetted by the sterilizing agent while simultaneously reducing the consumption of the sterilizing agent itself and reducing the energy requirements of the sterilizing process as a whole. Optimally, a wet aseptic process which makes use of a sterilizing agent having less toxicity when compared to peroxide, while achieving the above-discussed improvements in efficiency, has long been sought as a desirable substitute for previous processes.

SUMMARY OF THE INVENTION

The present invention overcomes the above-briefly discussed and other deficiencies and disadvantages of the prior art by providing an improved wet aseptic process which permits an absolutely reliable sterilization of the entire internal surface area of a container destined to receive food stuffs within an extremely short time and with extremely low consumption of sterilizing agent and energy. The present invention also contemplates apparatus for use in the practice of this novel technique.

In accordance with the present invention a sterilizing agent is atomized through the use of ultrasonic energy in order to provide extremely small droplets. These droplets, entrained in a stream of carrier gas, are subsequently electrically charged and thereafter electrostatically deposited on to the surfaces of the container to be sterilized. Thus, pursuant to the present invention, optimum sterilization of the entire surface area of a container is obtained through the use of a sterilizing agent which is ultrasonically atomized to form a mist, charged and subsequently directed to the surface to be sterilized by an electrostatic field. The electrostatic field causes the exceedingly small charged droplets which form the mist of sterilizing agent to be conveyed to the surface which is to be sterilized under directional control and within a very short time. The small interstitial areas which remain between these exceedingly small droplets which in theory remain unwetted, do not offer the micro-organisms which are to be destroyed sufficient room to evade the sterilizing agent. Restated, in view of the extremely small distances between droplets, and considering an example where hydrogen peroxide is employed as the sterilizing agent, the atomic oxygen which is formed as the $H_2O_2$ decomposes will, within a short distance and before such atomic oxygen has time to recombine to form an oxygen molecule, encounter any micro-organism which may be present in the interstitial areas. This may be contrasted with the prior art wherein the droplets deposited on the wall of a container to be sterilized would typically be in the range of 50-150 $\mu$m and thus the atomic oxygen frequently forms at such a large distance from the nearest micro-organism that it recombines to form oxygen molecules before being able to exercise its sterilizing action.

Apparatus in accordance with the preferred embodiment of the present invention employs, in order to impart an electrical charge to the ultrasonically atomized sterilizing agent, a corona discharge and particularly a point-type discharge. Apparatus in accordance with the invention also utilizes ultrasonic atomization at frequencies in the MHz range to produce droplets having diameters which are less than 10 $\mu$m and preferably in the range of 2-4 $\mu$m.

Also in accordance with the present invention, the electric field which causes the charged droplets to be attracted to the wall of a container to be sterilized, the container being comprised of a non-conductive material, is created through the use of a first electrode which is located outside of and surrounding the container and a second electrode of electrodes positionable within the container, the field being created in the gap between the inner and outer electrodes.

The present invention also contemplates the use, as a sterilizing agent, of a solution of hydrogen peroxide. Alternatively, a material to which germicidal properties are imparted by the passage of an ultrasonically atomized mist thereof through a corona discharge may be employed as the sterilizing agent. Examples of the latter type of material are distilled water and an aqueous solution of acetic acid.

BRIEF DESCRIPTION OF THE DRAWING

The present invention may be better understood and its numerous objects and advantages will become apparent to those skilled in the art by reference to the accompanying drawing wherein like reference numerals refer to like elements in the several FIGURES and in which.

DESCRIPTION OF THE DISCLOSED EMNBODIMENTS

Figure 1:
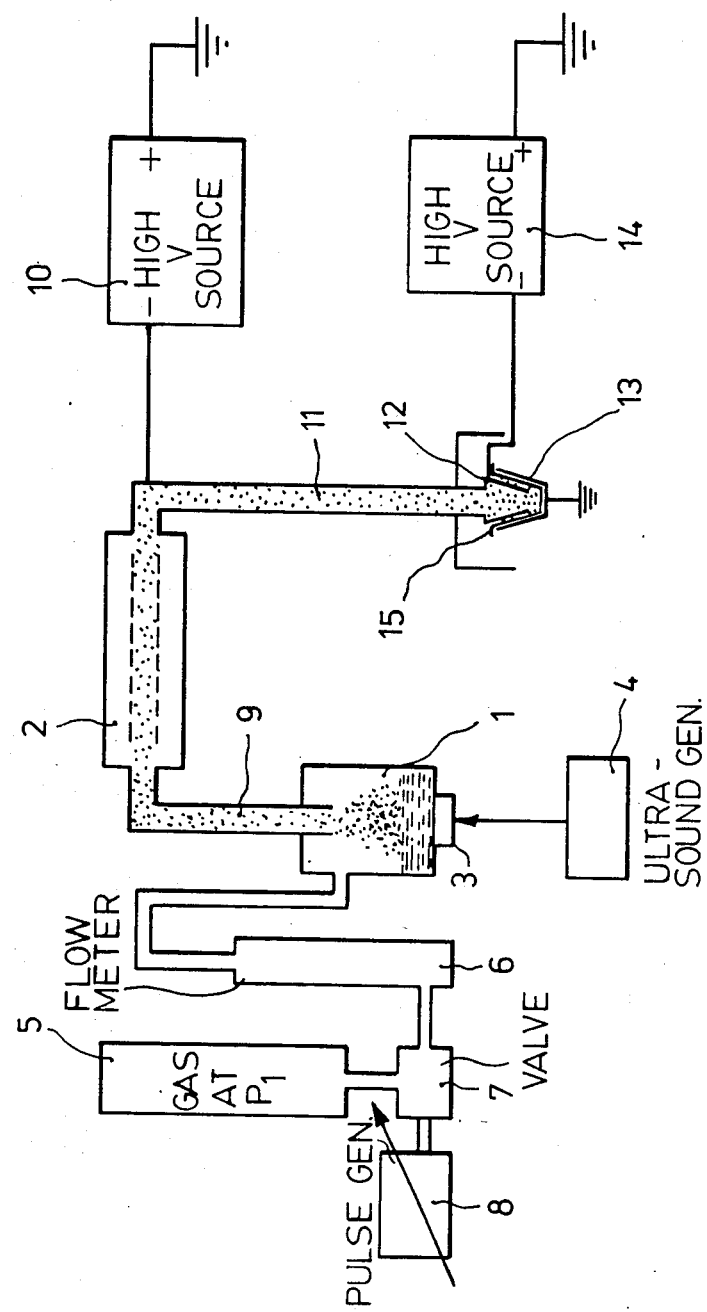
FIG. 1 is a schematic illustration of apparatus for use in the practice of a first embodiment of the present invention.

With reference now to the drawing, a sterilizing system in accordance with a first embodiment of the present invention is shown schematically in FIG. 1. The system of FIG. 1, as well as those of the other embodiments of the invention, includes an aerosol generator. The aerosol generator comprises a vessel 1 which is partially filled with a sterilizing agent in liquid form. The liquid in vessel 1 is atomized by being agitated at a frequency in the ultrasound range. As the apparatus is shown in FIG. 1, one or more ultrasound transducers 3 are coupled to the bottom of vessel 1. The transducers 3 are energized by electrical signals, in the range of 1 to 5 MHz provided by an ultrasound frequency signal generator 4. The energization of the ultrasound transducers 3 results in the creation of "acoustic effervescence" or "geysers" in the areas where the liquid sterilizing agent is subjected to an intense acoustic field. This results in the liquid being atomized to form very fine droplets. The efficiency of the atomization process is enhanced by the effect of small, vibrating gas bubbles. Tests have shown that, for example, when the ultrasound transducers 3 are energized at a frequency of 1.75 MHz the maximum of the diameter/frequency-of-occurrence distribution of the droplets which are formed lies at approximately 3 $\mu$m.

The mist formed by the ultrasonic agitation of the liquid sterilizing agent in vessel 1 is entrained in a stream of air or other suitable carrier gas. The carrier gas may be supplied from a pressurized reservoir, as indicated at 5, or by a blower. The carrier gas stream can be modulated, in any desired fashion, by means of a variable pulse generator 8 which provides control signals to a solenoid operated valve 7. By way of example, the modulation may comprise periodically interrupting the flow of carrier gas to thereby control the quantity of sterilizing agent to be deposited on a container to be sterilized. The gas flow rate may be measured by means of a flowmeter 6, which may be a rotary flowmeter, and adjusted to give the optimum aerosol concentration.

The mist, i.e., the ultrasonically atomized liquid sterilizing agent entrained in the carrier gas, leaves the aerosol generator vessel 1 by means of a "chimney" 9. The next step in the process is to impart an electrical charge to the droplets comprising the mist. In the embodiment of FIG. 1 the droplets are charged by being passed through a corona discharge in a charging section 2. Charge carriers, typically electrons, are generated by a point discharge about a first electrode which is arranged co-axially with and projects into a conductive metal conduit which functions as a second electrode. In order to produce the requiste field intensity, a high voltage source 10, which provides an output voltage in the 20-50 kV range, is connected so that the output potential of high voltage source 10 will appear between the electrode and the coaxial second electrode.

Within the charging section 2, the gas surrounding the tip of the first electrode, which will usually be connected to the negative polarity terminal of voltage source 10, is ionized. The positive gas ions thus formed are attracted to the electrode while the droplets which are flowing past the first electrode are charged by both the primary and by secondary electrons. Thus, in the disclosed embodiment, the droplets acquire a negative charge. The mist comprising the negatively charged droplets flows, via conduit 11, to the sterilizing section or precipitating head where the droplets are, in the manner to be described below, deposited on the inner surfaces of a container 15 which is to be sterilized.

The discharge end of conduit 11 is formed of or coated with an electrically conductive material, i.e., is metalized, so as to form an electrode 12. The electrode 12 functions as the first of a pair of generally concentric electrodes between which the containers to be sterilized will be positioned. Electrode 12, i.e., the inner of the two concentric electrodes, will be maintained at a negative potential in the case where a negative charge has been imparted to the droplets. Accordingly, electrode 12 is connected to a further high voltage source 14. The outer of the two concentric electrodes, which is indicated at 13, is at ground potential in the disclosed embodiment.

The negatively charged aerosol droplets will be discharged from the end of conduit 11 and will be forced to flow upwardly through the gap between electrode 12 and the inside wall of container 15. The electric field which is established between electrodes 12 and 13 will cause the droplets to move outwardly and thus be deposited on the inside surfaces of the container 15. The voltage supplied by high voltage source 14 is adjusted to optimize the rate at which the aerosol is deposited and to obtain the desired deposition time. The container 15 will be formed of a non-conductive material, typically a plastic, and a surface charge will build up thereon as the droplets are deposited. This surface charge will progressively reduce the effect of the field between electrodes 12 and 13 on the charged droplets and, most importantly, will guarantee that a uniform coating of the container is obtained.

Figure 2:
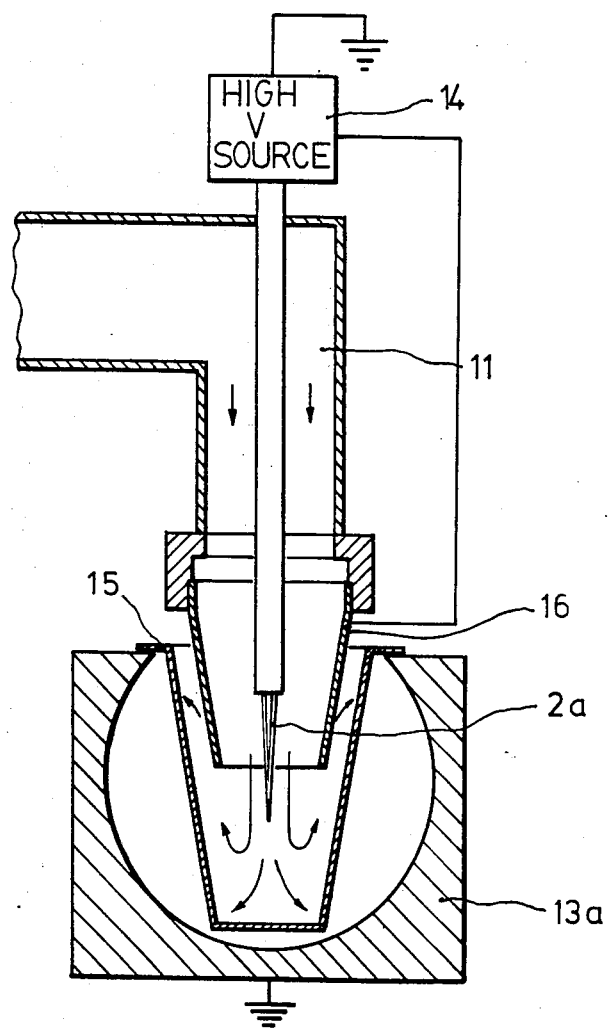
FIG. 2 is an enlarged, partial, cross-sectional, side-elevation view of apparatus in accordance with a second embodiment of the invention.

Referring now to FIG. 2, the embodiment partially shown therein differs from that of FIG. 1 by the elimination of the charging section 2. In the FIG. 2 embodiment the mist which flows through conduit 11 is uncharged. The charging of the droplets comprising the aerosol is achieved, in the FIG. 2 embodiment, through the use of electrode 2a. The tip of electrode 2a is positioned centrally with respect to an outer electrode 13a and functions as a point source of electrons. The container to be sterilized will be positioned in the cavity defined by electrode 13a and, as shown, this cavity is advantageously of spherical shape. Electrode 13a will be maintained at ground potential and a high voltage, typically a negative potential, will be applied to electrode 2a from the high voltage source 14. A strong electrostatic field which extends between the tip of electrode 2a and the wall of the cavity defined by electrode 13a will thus be established. Accordingly, the arrangement of FIG. 2, electrode 2a will, because of the corona discharge about the tip thereof, function to both negatively charge the droplets comprising the mist and to establish the field which causes these droplets to precipitate on the surface of the container 15.

The efficiency of the apparatus of FIG. 2 is enhanced through the use of an auxiliary electrode 16 which has a shape complementary to that of the upper portion of the container 15 to be sterilized. Electrode 16 is maintained at the same potential as the point electrode 2a and is suspended from conduit 11 and is insultated therefrom. The auxiliary electrode 16 functions as a funnel, which guides the aerosol droplets into the region where they will be charged by the action of the point source 2a, and further acts to shape the electrostatic field to which the charged droplets are exposed whereby the droplets are prevented from escaping upwardly out of the container 15 and are caused to be deposited in the upper region of the container.

Figures 3, 4:
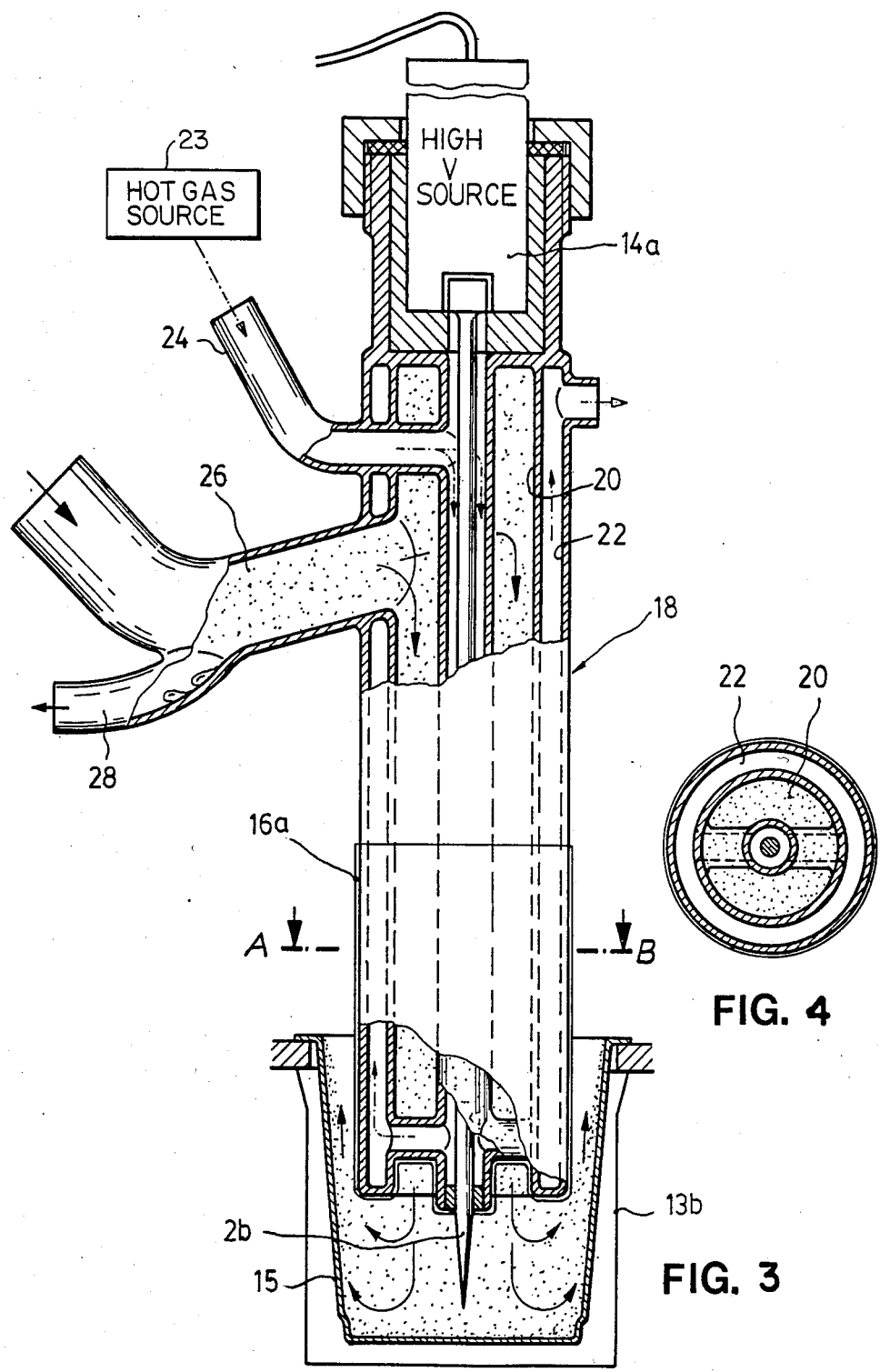
FIG. 3 is a cross-sectional, side-elevation view, partly in section, of a modified version of the apparatus of FIG. 2.
FIG. 4 is a cross-sectional view, taken along line A-B, of the apparatus of FIG. 3.

The embodiment of FIGS. 3 and 4 operates on the same principle as that of FIG. 2 and thus includes an electrode 2b, which functions as a point source of electrons, and a grounded outer electrode 13b which defines a cavity into which the container 15 to be sterilized is positioned. The electrode 2b is connected to a high voltage source 14a and is mounted in a precipitating head which may, for example, include in impact-resistant glass body. Electrode 2b is electrically connected to a metal foil which defines an auxiliary electrode 16a which surrounds the glass body at the lower end thereof and functions as the auxiliary electrode. The auxiliary electrode 16a, rather than being a metal foil, may be comprised of a conductive metal film deposited on the glass body of the precipitating head.

In a typical mode of operation, droplets of sterilizing agent continually produced in an aerosol generator of the type shown schematically in FIG. 1 are cyclically delivered to container 15, i.e., the ultrasonically atomized droplets are entrained in a modulated gas stream. The flow of the carrier gas is controlled, for example through the use of valve 7 of FIG. 1, so that pulses of atomized sterilizing agent having a length selected to optimize the treatment and to control the quantity of sterilizing agent deposited are formed.

The precipitating head of the embodiment of FIGS. 3 and 4 is doubled-walled and defines an inner passage 20 to which the atomized sterilizing agent is delivered via conduit 26. The precipitating head also defines an outer passage 22 through which a stream of heated air or other gas will be delivered from a source of heated gas indicated schematically at 23 via conduit 24. The gas supplied via conduit 24 will typically be heated to approximately 50° C. The purpose of the heated gas delivered via conduit 24 is to warm the walls of the passage 20 in the precipitating head whereby the atomized sterilizing agent will not condense on these walls and subsequently flow downwardly into a container being sterilzed. As an alternative to the use of a double-walled precipitating head and a supply of heated gas, the flow passage 20 may be surrounded by an electric heating element.

It is, of course, possible that droplets of the sterilizing agent may form on the wall of the supply conduit to the precipitating head. In order to prevent such droplets from entering the head the supply conduit 26, immediately upstream of the precipitating head, is angled upwardly. A drain passage 28 which communicates with conduit 26 will collect any liquid which forms on the wall of the conduit 26.

As will be obvious, means must be provided to produce relative movement between the precipitating head and, for example, electrode 13, 13a, 13b in all of the embodiments of the disclosed invention, electrodes 13, 13a, 13b defining the cavity into which the containers to be sterilized is placed. The means for producing such relative movement, which would be in the vertical direction as the apparatus is shown in FIGS. 1–3, is not shown in the drawing.

As will also be obvious to those skilled in the art, subsequent to the coating of the containers with the charged droplets as described above, it will in most cases be deemed desirable to subject the containers to a heat treatment to volatize any toxic sterilizing agent which may remain on the surfaces of the container. Such heat treatment can be accomplished by directing a stream of hot, sterile air or other gas against the surface of the container or through the use of microwave heating.

The sterilizing agent employed in the practice of the present invention, i.e., the liquid which is used to partially fill the vessel 1, may be hydrogen peroxide, $H_2O_2$. Alternatively, the sterilizing agent can be a fluid which has the capability of functioning as a sterilizing agent subsequent to atomization and passage through a corona discharge. Fluids which become chemically active as a result of being subjected to a corona discharge include atomized distilled water entrained in an air stream and atomized aqueous acetic acid entrained in a suitable carrier gas. In the case of distilled water, the destruction of micro-organisms results from the action of ozone and nitrogen ions formed in the vacinity of the source of electrons, i.e., in the corona discharge. In the cae of aqueous acetic acid, passage of the atomized sterilizing agent through the corona discharge results in the formation of peracetic acid. Peracetic acid is a suitable sterilizing agent in relatively small concentrations.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A process for sterilizing containers comprising the steps of:
   agitating a liquid sterilizing agent at an ultrasonic frequency to cause atomization thereof whereby droplets are formed in a first zone;
   entraining the atomized sterilizing agent in a carrier gas stream;
   imparting an electrical charge to the droplets of atomized sterilizing agent; and
   depositing the charged droplets of atomized sterilizing agent on a surface of a container to be sterilized under the influence of an electrostatic field by positioning the container to be sterilized within a cavity defined by a first electrode, positioning a second electrode at least partly within the container to be sterilized, and establishing the electrostatic field in a second zone distinct from said first zone, said second zone being located between the first and second electrodes.

2. The process of claim 1 wherein the step of agitating the liquid sterilizing agent comprises subjecting the sterilizing agent to ultrasonic energy at a frequency which produces droplets having diameters of less than 10 μm.

3. The process of claim 2 wherein the step of imparting an electrical charge to the droplets of atomized sterilizing agent comprises passing the stream of carrier gas and entrained droplets through a corona discharge.

4. The process of claim 3 further comprising:
   modulating the stream of carrier gas prior to entrainment of the atomized sterilizing agent.

5. The process of claim 4 wherein the step of modulating the carrier gas stream comprises
   periodically interrupting the flow of carrier gas to control the quantity of sterilizing agent to be deposited on the container to be sterilized.

6. The process of claim 5 further comprising:
   passing the entrained droplets of sterilizing agent through a heated conduit prior to imparting said electrical charge to the droplets whereby condensation of the droplets prior to their being charged is prevented.

7. The process of claim 3 further comprising:
   passing the entrained droplets of sterilizing agent through a heated conduit prior to imparting said electrical charge to the droplets whereby condensation of the droplets prior to their being charged is prevented.

8. The process of claim 3 wherein the sterilizing agent is selected from the group consisting of peroxides, acetic acid and distilled water.

9. The process of claim 1 wherein the step of imparting an electrical charge to the droplets of atomized sterilizing agent comprises passing the stream of carrier gas and entrained droplets through a corona discharge.

10. The process of claim 9 further comprising the steps of:
    selecting a material in liquid form which has the capability of functioning as a sterilizing agent subsequent to passage through a corona discharge; and
    delivering the selected material to a vessel where the selected material is said liquid sterilizing agent.

11. The process of claim 1 further comprising:
    passing the entrained droplets of sterilizing agent through a heated conduit prior to imparting an electrical charge to the droplets whereby condensation of the droplets prior to their being charged is prevented.

12. The process of claim 1 further comprising:
    modulating the stream of carrier gas prior to entrainment of the atomized sterilizing agent.

13. The process of claim 12 wherein the step of modulating the carrier gas stream comprises:
    periodically interrupting the flow of carrier gas to control the quantity of sterilizing agent to be deposited on the container to be sterilized.

14. The process of claim 1 wherein the sterilizing agent is selected from the group consisting of peroxides, acetic acid and distilled water.

15. The process of claim 1 wherein the electrical charge is imparted to the droplets in a third zone distinct from said first and second zones.

16. Apparatus for use in the sterilization of containers comprising:
    means for agitating a liquid sterilizing agent at a frequency in the ultrasound range to cause the atomization thereof whereby droplets are formed;
    means for entraining the atomized sterilizing agent in a stream of carrier gas;
    means for generating free electrons;
    means for directing the stream of carrier gas with entrained droplets of sterilizing agent past said means for generating free electrons whereby the droplets of sterilizing agent will become electrically charged;
    first electrode means, said first electrode means defining a cavity adapted for receiving a container to be sterilized;
    second electrode means, said second electrode means being configured to at least in part project into the cavity defined by said first electrode means so that the container to be sterilized is located between said first and second electrode means;
    means for applying a high voltage to said second electrode means to produce an electrostatic field between said first and second electrode means; and
    means for directing the stream comprising carrier gas with entrained charged droplets of sterilizing agent into a container to be sterilized received in said first electrode means defined cavity whereby the charged droplets will be directed onto a surface of the container.

17. The apparatus of claim 16 wherein said means for directing the stream of carrier gas with entrained charged droplets includes a conduit through which said stream is discharged into the container to be sterilized and wherein said second electrode means at least in part defines the discharge end of the said conduit.

18. The apparatus of claim 17 further including:
means for heating at least a portion of said conduit to prevent condensation of droplets of sterilizing agent on the walls of said conduit.

19. The apparatus of claim 16 wherein said means for generating electrons comprises:
means establishing a corona discharge.

20. The apparatus of claim 16 wherein said entraining means includes:
means for modulating said stream of carrier gas and entrained droplets prior to the direction thereof past said means for generating free electrons.

21. The apparatus of claim 20 wherein said modulating means comprises:
a source of pressurized gas;
flow conduit means for flow communication between said source of pressurized gas and said entraining means; and
valve means interposed in said flow conduit means for controlling the flow of gas from sid source of pressurized gas to said entraining means.

22. The apparatus of claim 16 wherein said means for agitating comprises:
a vessel;
ultrasound transducer means coupled to said vessel; and
means for energizing said ultrasound transducer means.

23. The apparatus of claim 22 wherein said vessel contains a liquid selected from the group consisting of a peroxide, acetic acid and distilled water.

24. Apparatus for use in the sterilization of containers comprising:
means for agitating a liquid sterilizing agent at a frequency in the ultrasound range to cause the atomization thereof whereby droplets are formed;
means for entraining the atomized sterilizing agent in a stream of carrier gas;
first electrode means, said first electrode means defining a cavity adapted for receiving a container to be sterilized;
means for generating free electrons, said electron generating means including second electrode means, said second electrode means having at least a part projecting into the cavity defined by said first electrode means so that a container to be sterilized received in said cavity will be located between said first and second electrode means, said projecting part of said second electrode means terminating in a point;
means for establishing an electrostatic field between said first and second electrode means, said field establishing means applying a high voltage to said second electrode means whereby free electrons will be generated in the vicinity of said point termination of said second electrode means; and
means for directing the stream of carrier gas with entrained droplets of sterilizing agent past said point termination of said second electrode means whereby the droplets of sterilizing agent will become electrically charged and will be directed by said electrostatic field onto a surface of the container, said directing means defining a flow path for said stream and including third electrode means which defines the discharge end of a conduit through which said stream is discharged into the container, said third electrode means being generally coaxial with said second electrode means, said second electrode means extending into the said cavity a greater distance than said third electrode means.

25. The apparatus of claim 24 wherein said cavity defined by said first electrode means has a generally spherical shape.

26. The apparatus of claim 24 further comprising;
means for applying a voltage of the same polarity as applied to said second electrode means to said third electrode means.

27. The apparatus of claim 26 wherein said entraining means includes;
means for modulating said stream of said carrier gas and entrained droplets.

28. The apparatus of claim 27 wherein said means for directing further includes;
means for heating at least a portion of said flow path for the stream of carrier gas with entrained droplets of sterilizing agent.

29. The apparatus of claim 24 wherein said entraining means includes;
means for modulating said stream of said carrier gas and entrained droplets.

30. The apparatus of claim 29 wherein said means for directing further includes;
means for heating at least a portion of said flow path for the stream of carrier gas with entrained droplets of sterilizing agent.

31. The apparatus of claim 24 wherein said means for directing further includes;
means for heating at least a portion of said flow path for the stream of carrier gas with entrained droplets of sterilizing agent.

* * * * *